United States Patent [19]

Brezinski et al.

[11] 4,297,193
[45] Oct. 27, 1981

[54] PH ELECTRODE GLASS COMPOSITIONS

[75] Inventors: Donald P. Brezinski, Corning; Leroy R. Morse, Campbell, both of N.Y.

[73] Assignee: Corning Glass Works, Corning, N.Y.

[21] Appl. No.: 152,358

[22] Filed: May 22, 1980

[51] Int. Cl.$^3$ .......................... G01N 27/36; C03C 3/04
[52] U.S. Cl. .................. 204/195 G; 501/55; 501/73
[58] Field of Search ............... 204/195 G; 106/52

[56] References Cited
U.S. PATENT DOCUMENTS

| | | | |
|---|---|---|---|
| 2,444,845 | 7/1948 | Perley | 204/195 G |
| 2,497,235 | 2/1950 | Perley | 204/195 G |
| 3,372,104 | 3/1968 | Ross et al. | 106/52 |
| 3,410,777 | 11/1968 | Ross | 204/195 G |
| 3,433,749 | 3/1969 | Nishimoto et al. | 204/195 G |
| 3,480,536 | 11/1969 | Arthur | 204/195 G |
| 4,028,196 | 6/1977 | Young | 204/195 G |

*Primary Examiner*—G. L. Kaplan
*Attorney, Agent, or Firm*—William E. Maycock

[57] ABSTRACT

A glass composition for use in pH-responsive glass electrodes, and a glass electrode having a pH-responsive membrane of such glass, which composition consists essentially of (in mole percent on the oxide basis):

a. from about 30 to about 37 mole percent $Li_2O$;
b. from 0 to about 4 mole percent of at least one oxide selected from the group consisting of $Cs_2O$ and $Rb_2O$;
c. from about 2 to about 12 mole percent of at least one oxide selected from the group consisting of $La_2O_3$ and $Pr_2O_3$;
d. from about 2 to about 10 mole percent of at least one oxide selected from the group consisting of $Ta_2O_5$ and $Nb_2O_5$;
e. from 0 to about 4 mole percent $UO_2$; and
f. the balance $SiO_2$;

with the proviso that there is present in the composition at least about 2 mole percent of at least one oxide selected from the group consisting of $Pr_2O_3$ and $Nb_2O_5$.

22 Claims, No Drawings

PH ELECTRODE GLASS COMPOSITIONS

BACKGROUND OF THE INVENTION

This invention relates to pH electrode glass compositions. More particularly, this invention relates to pH electrode glass compositions having very low bulk resistivities and very low surface resistivities after aging in aqueous solutions.

Glass electrodes sensitive to the hydrogen ion activity, or pH, of a solution have been known for some time. Since their discovery in 1906 and the various modifications and improvements in glass compositions which followed, such electrodes have come to play an important role in both research and industry.

Desirable properties in a pH glass electrode, which largely are functions of the glass composition and configuration, include the following:

a. Low volume or bulk resistivity. Potentiometric error due to offset current and finite impedance at the input of the electrode potential measuring means, e.g., a pH meter, is directly proportional to the total resistance of the pH electrode. Consequently, low bulk resistivity in a pH glass allows fabrication of smaller or thicker membranes for such purposes as smaller size, increased strength, and attainment of required geometries, while retaining the good performance of the more common larger or thinner membranes.

b. Low surface resistivity. Decreased surface resistance reduces the tendency of pH electrodes to polarize. The term "polarize" is commonly used to describe the long-term disturbance of pH electrode potential often induced by a brief current flow through the sensing glass membrane. Because recovery from such disturbances typically is slow, for a period of time after a polarizing disturbance the pH measurement shows a slowly decaying error. The practical advantages of decreased surface resistance include enhanced speed of response, especially with high capacitance cables, faster decay of transient potentials induced by external electrostatic coupling, and faster stabilization after connection to the pH meter and after changing bathing solutions. These advantages are particularly important at low temperatures and with noncombination electrodes which do not have a low-impedance reference junction in the vicinity of the pH electrode to act as a sink for stray currents.

c. Near-theoretical slope (volts/pH unit). Maintenance of near-theoretical slope over the entire pH range of 0-14 simplifies calibration and allows pH measurements over the maximum range usually encountered.

d. Low sodium error. Low sodium error improves the accuracy of pH measurements in strongly alkaline solutions containing sodium ions.

e. Low asymmetry potential. Asymmetry refers to the potential difference across a membrane when the inner and outer surfaces are bathed with identical solutions. A low asymmetry potential generally is associated with enhanced stability and uniformly in the potentiometric characteristics of manufactured electrodes.

f. High chemical durability. The pH glass should have sufficient chemical durability to allow a long life in strongly acidic or alkaline solutions.

In general, it is not possible to obtain a single pH glass in which all of the desirable properties have been optimized. There usually is a degree of compromise associated with any pH glass electrode, with the end use or uses dictating which properties are of the greatest importance. For example, the more recent pH glasses emphasize such properties as low sodium error, low bulk resistivity, improved workability, enhanced durability, and the absence of devitrification or phase separation. The most significant of these more recent pH glasses are described below.

U.S. Pat. No. 3,372,104 broadly discloses pH electrode glass compositions which are lithia-silicate glasses provided from a pre-melt composition or mixture according to the following formula, expressed in ranges of mole percentages on the oxide basis: (1) about 27-29 mole percent $Li_2O$, (2) about 2-4 mole percent of at least one material selected from the group consisting of $Cs_2O$ and $Rb_2O$, (3) about 4-7 mole percent of at least one rare earth metal oxide, (4) about 1-3 mole percent $UO_2$ and/or about 1-3 mole percent $Ta_2O_5$, and (5) the balance $SiO_2$ which typically is about 58-63 mole percent. The only rare earth metal oxide actually used was $La_2O_3$.

Glasses similar to the above are claimed in U.S. Pat. No. 3,410,777 and have a composition consisting essentially of about 27-29 mole percent $Li_2O$, about 2-4 mole percent of at least one material selected from the group consisting of $Cs_2O$ and $Rb_2O$, about 4-7 mole percent of at least one rare earth metal oxide, about 1-3 mole percent $UO_2$, and the balance $SiO_2$. Although the only rare earth metal oxide actually used was $La_2O_3$, the rare earth metal oxide can be selected from the group consisting of $La_2O_3$ and $Pr_2O_3$.

Finally, U.S. Pat. No. 4,028,196 discloses pH electrode glass compositions consisting essentially of 30-40 mole percent $Li_2O$, 50-60 mole percent $SiO_2$, 2-8 mole percent $La_2O_3$, 2-8 mole percent $Ta_2O_5$, and 0-3 mole percent $Cs_2O$, wherein the sum of the mole percentages of $Li_2O$ and $Ta_2O_5$ is equal to or greater than 34.

Glass compositions such as those described above have proven satisfactory for the construction of pH glass electrodes having a general utility. For miniature, rugged, or flat-membrane pH glass electrodes, however, there still is a need for glass compositions having very low bulk and surface resistivities and, as a consequence, a reduced tendency to polarize.

SUMMARY OF THE INVENTION

It therefore is an object of the present invention to provide a pH-sensitive glass composition having very low bulk resistivity and very low surface resistivity after aging in aqueous solutions.

It also is an object of the present invention to provide a glass electrode having a pH-responsive membrane of glass having very low bulk resistivity and very low surface resistivity after aging in aqueous solutions.

These and other objects will be apparent to those having ordinary skill in the art from a consideration of the specification and claims which follow.

It has been discovered that glasses containing certain rare earth metal oxides, notably praesodymium oxide, and certain group 5b metal oxides exhibit properties that are particularly desirable in certain pH electrode applications, i.e., pH electrodes having very small or thick sensing membranes. These properties include very low surface and bulk electrical resistivities, good workability, and fast and accurate electrode response to changes in pH. Such properties, of course, are desirable for traditional pH electrode applications as well. Thus, the glasses of this invention have been found to be particularly advantageous for use in miniature, rugged, and flat-membrane electrodes, but are not limited to such uses.

Accordingly, the present invention provides a glass composition for use in pH-responsive glass electrodes, and a glass electrode having a pH-responsive membrane of such glass, which composition consists essentially of (in mole percent on the oxide basis):
a. from about 30 to about 37 mole percent $Li_2O$;
b. from 0 to about 4 mole-percent of at least one oxide selected from the group consisting of $Cs_2O$ and $Rb_2O$;
c. from about 2 to about 12 mole percent of at least one oxide selected from the group consisting of $La_2O_3$ and $Pr_2O_3$;
d. from about 2 to about 10 mole percent of at least one oxide selected from the group consisting of $Ta_2O_5$ and $Nb_2O_5$;
e. from 0 to about 4 mole percent $UO_2$; and
f. the balance $SiO_2$;

with the proviso that there is present in the composition at least about 2 mole percent of at least one oxide selected from the group consisting of $Pr_2O_3$ and $Nb_2O_5$.

DETAILED DESCRIPTION OF THE INVENTION

The phenomena of surface resistance and polarization can be explained, in simplified terms, as follows. The total electrical resistance of a hydrated or aged pH glass membrane is the sum of two components, an interior or bulk resistance and a surface resistance. In the interior of the glass, current is carried by highly mobile alkali metal ions (generally lithium ions in modern compositions and in the compositions of the present invention) which move relative to fixed siloxy sites having a negative charge. Near the glass surface, however, current is carried by hydrogen ions rather than by lithium ions. When a pH glass is immersed in an aqueous solution, lithium ions progressively diffuse out of the glass surface and are replaced by hydrogen ions which have a much higher affinity for the fixed negative sites but much lower site-to-site mobility. As a consequence of the lower hydrogen ion mobility, the bulk resistivity of the interior portions of the ion-exchanged glass surface exceeds the resistivity of the native, interior glass by a factor of at least a thousand. The outer portions of the ion-exchanged surfaces, however, are hydrolyzed into much more permeable silica-gel networks of low resistivity. Thus, during exposure to an aqueous environment, a very thin barrier layer of high resistivity glass progressively develops near each surface at the interface between the more conductive bulk glass and the silica-gel phases. For a more detailed discussion of the properties of hydrated pH glass surfaces, see, e.g., R. P. Buck, *J. Electroanal. Chem.*, 18, 363 (1968), and A. Wikby, *Physics and Chemistry of Glasses*, 15, 37 (1974).

The electrical properties of the hydrated pH glass membrane can be approximated by the following idealized circuit model. The resistance of the bulk glass portion of the membrane can be represented by a fixed resistor, $R_b$. The high-resistance barrier layers separating the bulk glass and the surface gel layers are quite thin and, therefore, are electrically analogous to capacitors with a "leaky" (finite resistance) dielectric. Thus, the simplest circuit model which approximates the electrical behavior of a hydrated pH glass membrane consists of a resistor $R_b$ which is connected in series with a combination of a resistor $R_s$ and a capacitor $C_s$ connected in parallel, in which $\frac{1}{2} R_s$ and $2 C_s$ represent the resistance and capacitance contributions, respectively, of each surface.

The above idealized electrical model correctly predicts a time-variant shift in potential when a direct current pulse is passed through a pH glass membrane. The graphical representation of a direct current pulse of fixed magnitude and duration is, of course, rectangular in waveform. When such a current pulse is passed through a new or hydrogen fluoride-etched pH glass membrane which has no surface resistance, the induced voltage waveform also is rectangular and has a magnitude which is proportional to the bulk resistance of the membrane. In an aged, i.e., hydrated, membrane having surface resistance layers, however, such surface layers result in an additional, time-varying component in the induced voltage. Thus, the induced voltage rises abruptly to a magnitude which is proportional to the membrane glass bulk resistance. But the induced voltage then continues to rise nonlinearly and more slowly with time by an additional magnitude which is proportional to the sum of the resistances of the two surface layers. When the direct current pulse is terminated, the induced voltage drops abruptly to a magnitude which is proportional to the sum of the resistances of the surface layers. This residual induced voltage then continues to drop nonlinearly with time, eventually returning to zero.

This nonlinear, delayed reduction of membrane potential is the phenomenon commonly referred to as polarization, which phenomenon is of special significance. As a consequence of surface resistance, a brief electrical disturbance passing current through a pH glass membrane has a long-term residual effect on the measured electrode potential.

Electrical disturbances commonly are encountered during normal pH electrode usage. For example, pH membranes routinely are subjected to polarizing currents as a consequence of direct charge transfer during handling, remote electrostatic coupling with charged worker apparel, and charging of electrode cable capacitance to a new potential upon a change in pH. The adverse consequences of polarization susceptibility include greater measurement error, slower response, and enhanced noise.

The electrical resistance properties of a glass membrane are readily measured by noting the time-variant shift in electrical potential across the membrane which occurs in response to the application of a constant-current pulse. The bulk resistivity of the electrode glass is given by the expression, $$\rho_b = \frac{\Delta V_b A}{li}$$

where A is the membrane area, l is the membrane thickness, and $\Delta V_b$ is the instantaneous change in electrode potential upon application of current i. Similarly, the surface resistivity of the electrode membrane can be expressed as $$\rho_s = \frac{\Delta V_s A}{i}$$

where $\Delta V_s$ is the change in electrode voltage during a fixed time interval after application of the current i.

As already indicated, the present invention broadly provides a glass composition for use in pH-responsive glass electrodes consisting essentially of (in mole percent on the oxide basis):
a. from about 30 to about 37 mole percent $Li_2O$;
b. from 0 to about 4 mole percent of at least one oxide selected from the group consisting of $Cs_2O$ and $Rb_2O$;
c. from about 2 to about 12 mole percent of at least one oxide selected from the group consisting of $La_2O_3$ and $Pr_2O_3$;
d. from about 2 to about 10 mole percent of at least one oxide selected from the group consisting of $Ta_2O_5$ and $Nb_2O_5$;
e. from 0 to about 4 mole percent $UO_2$; and
f. the balance $SiO_2$;
with the proviso that there is present in the composition at least about 2 mole percent of at least one oxide selected from the group consisting of $Pr_2O_3$ and $Nb_2O_5$.

In a preferred embodiment, such glass composition consists essentially of:
a. from about 30 to about 37 mole percent $Li_2O$;
b. from 0 to about 4 mole percent of at least one oxide selected from the group consisting of $Cs_2O$ and $Rb_2O$;
c. from 0 to about 6 mole percent $La_2O_3$;
d. from about 2 to about 8 mole percent $Pr_2O_3$;
e. from about 2 to about 8 mole percent of at least one oxide selected from the group consisting of $Ta_2O_5$ and $Nb_2O_5$;
f. from 0 to about 4 mole percent $UO_2$; and
g. the balance $SiO_2$;
with the proviso that the sum of the mole percentages of $La_2O_3$ and $Pr_2O_3$ is equal to or less than about 12.

In another preferred embodiment, such glass composition consists essentially of:
a. from about 30 to about 37 mole percent $Li_2O$;
b. from 0 to about 4 mole percent of at least one oxide selected from the group consisting of $Cs_2O$ and $Rb_2O$;
c. from about 2 to about 8 mole percent $La_2O_3$;
d. from 0 to about 6 mole percent $Ta_2O_5$;
e. from about 2 to about 8 mole percent $Nb_2O_5$;
f. from 0 to about 4 mole percent $UO_2$; and
g. the balance $SiO_2$;
with the proviso that the sum of the mole percentages of $Ta_2O_5$ and $Nb_2O_5$ is equal to or less than about 10.

In a more preferred embodiment, such glass composition consists essentially of:
a. from about 31 to about 35 mole percent $Li_2O$;
b. from about 1 to about 3 mole percent of at least one oxide selected from the group consisting of $Cs_2O$ and $Rb_2O$;
c. from 0 to about 4 mole percent $La_2O_3$;
d. from about 3 to about 6 mole percent $Pr_2O_3$;
e. from about 4 to about 8 mole percent of at least one oxide selected from the group consisting of $Ta_2O_5$ and $Nb_2O_5$;
f. from 0 to about 2 mole percent $UO_2$; and
g. the balance $SiO_2$.

In another more preferred embodiment, such glass composition consists essentially of:
a. from about 31 to about 35 mole percent $Li_2O$;
b. from about 1 to about 3 mole percent of at least one oxide selected from the group consisting of $Cs_2O$ and $Rb_2O$;
c. from about 3 to about 7 mole percent $La_2O_3$;
d. from 0 to about 4 mole percent $Ta_2O_5$;
e. from about 2 to about 7 mole percent $Nb_2O_3$;
f. from 0 to about 2 mole percent $UO_2$; and
g. the balance $SiO_2$;
with the proviso that the sum of the mole percentages of $Ta_2O_5$ and $Nb_2O_5$ is equal to or less than about 10.

The present invention is further illustrated, but not limited, by the examples which follow. In the examples, pre-melt compositions are shown. Each component is expressed in terms of the mole percentage of a specific oxide for the sake of clarity and simplicity. It is to be understood, however, that the components of any given glass composition can be selected from any compound which will yield an oxide upon fusion. For example, lithium carbonate often is preferred over lithium oxide as a pre-melt component because of its availability and relative inertness. Thus, carbonates, hydroxides, nitrates, and other such compounds, as well as oxides, can be used.

Each glass was prepared by mixing the pure raw materials in the dry state and melting the resulting mixture in a platinum crucible at 1500° C. for five hours, typically in an electric muffle furnace, with intermittant mixing. Other temperatures, e.g., from about 1100° to about 1700° C., and heating times, e.g., from about 1 to about 7 hours, can be employed, however, as is well known by those having ordinary skill in the art.

Glass membranes then were prepared in accordance with well-known procedures. Typically, one end of a pre-heated glass tubing having the appropriate coefficient of expansion and softening point was dipped into the molten pH electrode glass composition contained in a platinum crucible and then withdrawn. In the case where a bulbous membrane was desired, the molten glass adhering to the tubing was blown to the desired size and shape.

EXAMPLES 1–11

Pre-melt compositions for a number of glasses, exemplifying some preferred glasses and additional glasses which illustrate the broader limits of the present invention, are shown in Table I. This table also includes four prior art or control glasses which are given letter designations.

TABLE I

Pre-Melt Compositions of Various pH Glasses

| Example or Control | Composition (Mole Percent) | | | | | | | | | | |
|---|---|---|---|---|---|---|---|---|---|---|---|
| | $Li_2O$ | $Cs_2O$ | $Rb_2O$ | $BaO$ | $La_2O_3$ | $Pr_2O_3$ | $CeO_2$ | $Ta_2O_5$ | $Nb_2O_5$ | $UO_2$ | $SiO_2$ |
| 1 | 33 | 2 | | | | 6 | | 6 | | | 53 |
| 2 | 33 | 2 | | | | 6 | | 6 | | 2 | 51 |
| 3 | 33 | 2 | | | 3 | 3 | | 6 | | | 53 |
| 4 | 33 | 2 | | | 6 | | | 3 | 3 | | 53 |
| 5 | 33 | 2 | | | 6 | | | | 6 | | 53 |
| 6 | 33 | | 2 | | 6 | | | | 6 | | 53 |
| 7 | 29 | 2 | | | 2 | | | 2 | | | 65 |

TABLE I-continued

Pre-Melt Compositions of Various pH Glasses

| Example or Control | Composition (Mole Percent) | | | | | | | | | | |
|---|---|---|---|---|---|---|---|---|---|---|---|
| | $Li_2O$ | $Cs_2O$ | $Rb_2O$ | $BaO$ | $La_2O_3$ | $Pr_2O_3$ | $CeO_2$ | $Ta_2O_5$ | $Nb_2O_5$ | $UO_2$ | $SiO_2$ |
| 8 | 33 | 2 | | | | 2 | | 8 | | | 55 |
| 9 | 37 | 2 | | | | 8 | | 8 | | | 45 |
| 10 | 30 | | | | | | 6 | 6 | | | 58 |
| 11 | 33 | 2 | | | | | 6 | | 6 | | 53 |
| A | 33 | 2 | | | 6 | | | 6 | | | 53 |
| B | 30 | | | | 6 | | | 6 | | | 58 |
| C | 28 | 2 | | 5 | 2 | | | | | | 63 |
| D | 24.4 | | | 7 | 2.5 | | 4.5 | | | | 61.6 |

Control glasses A and B are typical of the compositions disclosed in U.S. Pat. No. 4,028,196. Control glasses C and D are representative of the compositions disclosed in U.S. Pat. Nos. 2,444,845 and 3,480,536, respectively.

Table II summarizes electrical resistance properties of the glasses of Table I, although not all properties were determined for each glass. Other properties for these glasses are summarized in Table III.

TABLE II

Electrical Resistance Properties of Various pH Glasses

| Example or Control | Bulk Glass Resistivity[a] | Acid-Aged Sensors[b] Surface Resistivity[c] | | Base-Aged Sensors[b] Surface Resistivity[c] | |
|---|---|---|---|---|---|
| | | 0° C. | 25° C. | 0° C. | 25° C. |
| 1 | 9.0 | 1900 | 74 | 470 | 88 |
| 2 | 8.9 | 1800 | 68 | 1600 | 110 |
| 3 | 9.1 | 2100 | 86 | 2600 | 180 |
| 4 | 9.2 | 2000 | 67 | 2500 | 111 |
| 5 | 9.2 | 3100 | 110 | 2900 | 159 |
| 6 | 9.2 | 1900 | 64 | 3000 | 140 |
| 7 | 9.6 | | | | |
| 8 | 8.4 | 780 | 30 | 2500 | 160 |
| 9 | 8.4 | | | | |
| 10 | 9.0 | 2600 | 110 | 3000 | 260 |
| 11 | 9.0 | | | | |
| A | 9.2 | 3000 | 140 | 4700 | 120 |
| B | 9.2 | 3400 | 130 | 2600 | 180 |
| C | 10.5 | 6400 | 370 | | |
| D | 11.3 | 9000 | 610 | 23000 | 1300 |

[a]Log D.C. bulk resistivity in ohm-cm, determined at about 25° C. for untreated glass.
[b]Data from operational electrode assemblies after accelerated aging for 24 hours at 90° C. in 0.02 N $H_2SO_4$ (acid) or 0.01 N NaOH (base).
[c]Values in megohms-$cm^2$

TABLE III

Other Properties of Various pH Glasses

| Example or Control | Bulk Glass | | | Acid-Aged Sensors[a] | | | | Base-Aged Sensors[b] | | | |
|---|---|---|---|---|---|---|---|---|---|---|---|
| | Density (g/cc) | Chemical Durability | | Slope[e] (% Theoretical) | | Sodium error | Asymmetry[g] (MV) | Slope[e] (% Theoretical) | | Sodium error[f] | Asymmetry[g] (MV) |
| | | Acid[c] | Base[d] | pH 0-9 | pH 9-14 | | | pH 0-9 | pH 9-14 | | |
| 1 | 3.80 | 0.171 | 0.103 | 100.0 | 100.3 | 30 | −7 | 99.9 | 100.3 | 14 | 0 |
| 2 | 3.94 | 0.171 | 0.089 | 100.2 | 98.0 | 28 | −9 | 99.8 | 97.6 | 18 | 11 |
| 3 | 3.81 | 0.180 | 0.053 | 99.0 | 99.5 | 50 | −6 | 99.4 | 100.4 | 14 | −9 |
| 4 | 3.58 | 0.177 | 0.131 | 99.8 | 100.1 | 24 | −7 | 100.2 | 99.5 | 12 | −7 |
| 5 | 3.37 | 0.181 | 0.163 | 99.8 | 99.0 | 24 | −11 | 99.7 | 101.1 | 13 | −14 |
| 6 | 3.32 | 0.191 | 0.152 | 100.1 | 99.9 | 24 | −9 | 99.9 | 100.5 | 14 | −12 |
| 7 | | | | | | | | | | | |
| 8 | | | | 93 | 102 | 121 | −17 | 91 | 100 | 125 | −3 |
| 9 | | | | | | | | | | | |
| 10 | | | | 96 | 99 | 76 | −18 | 93 | 98 | 82 | 1 |
| 11 | | | | | | | | | | | |
| A | 3.80 | 0.174 | 0.120 | 100.0 | 98.5 | 27 | −19 | 99.5 | 99.7 | 11 | −1 |
| B | 3.71 | 0.149 | 0.046 | 99.7 | 99.0 | 56 | −18 | 99.1 | 99.7 | 48 | 84 |
| C | 2.95 | 0.349 | 0.425 | | | | | | | | |
| D | 3.17 | 0.051 | 0.078 | | | | | | | | |

[a]Data from operational electrode assemblies after accelerated aging for 24 hours at 90° C. in 0.02 N $H_2SO_4$ (acid).
[b]Data from operational electrode assemblies after accelerated aging for 24 hours at 90° C. in 0.01 N NaOH (base).
[c,d]Powder durability tests in [c]0.02 N $H_2SO_4$ (acid) and [d]0.01 N NaOH (base). Samples were prepared according to ASTM designation C225-73 in "Annual Book of ASTM Standards", Part 17, Sections 14–16, American Society for Testing and Materials, Philadelphia, 1978; analyses were carried out in accordance with the procedure of D. L. Rothermel and M. E. Nordberg, Ceramic Bulletin, 31, 324 (1952), except leachate volumes of 25 ml. were employed instead of 5 ml. Results are expressed as weight percent total alkali removed under the specified conditions, reported as equivalent weight percent $Na_2O$.
[e]Measured by comparison with a standard platinum hydrogen electrode in 1 M HCl, 1 M KOH, and 0.01 M borax buffer (pH 9.18).
[f]Measured by comparison with a standard platinum hydrogen electrode in 1 N NaOH.
[g]Measured in pH 7, 0.05 M phosphate buffer with an electrode filled with a similar solution.

As the data in Tables I–III show, the present invention provides pH glasses which exhibit especially low surface resistivities and which, as a consequence, are less susceptible to polarization. The glass of Example 1 has been found to be especially useful in the preparation of rugged and miniaturized electrodes requiring especially low electrical resistance properties and for flat membrane electrodes requiring good glass workability. The glasses of Examples 2–6, inclusive, and others related thereto in formulation, also are similarly useful for the construction of rugged, miniaturized, and flat membrane electrodes. The glasses of Examples 1–6, inclusive, have been found to perform well in conventional, bulb-type pH electrodes.

The acid-aged and base-aged data in Table II and the chemical durability data in Table III indicate the effects of accelerated aging in the respective reagents at 90° C. for 24 hours.

Table II shows the electrical resistivities of the glasses of the examples and the control glasses. Note that the glasses of Examples 1, 2, and 3 are lower in bulk resistivity than all of the control glasses. The glasses of Examples 4, 5, and 6 are as low in bulk resistivity as glass A, the control glass lowest in bulk resistivity. Acid-aged electrodes fabricated from the glasses of Examples 1, 2, 3, 4, and 6 exhibit surface resistivities at both 0° C. and 25° C. which are significantly lower than the corresponding resistivities of the control glass electrodes. In base-aged electrodes, the glasses of the first six examples exhibit surface resistivities at 0° C. which generally are lower than the corresponding resistivities of the control glasses. Thus, the glasses of the present invention typically have advantageous resistance properties, compared to the control glasses, under most conditions of use. For example, the low surface resistance values at 0° C. of the glasses of Examples 1–6 indicate that these glasses are especially well-suited for electrodes having low temperature applications.

Table III shows selected other properties which further characterize the glasses of the present invention and demonstrate the suitability of such glasses in the construction of operational pH electrodes. The tabulated chemical durability data indicate the total of all alkali metal oxide components extracted from pulverized glass samples exposed to the indicated solutions at 90° C. for four hours; preferred values are below about 0.20. The asymmetry potential was measured in pH 7.0 buffer solution; a satisfactory value is 0±about 20 mV.

Our findings can be summarized as follows. In general, current pH glasses incorporate $La_2O_3$ as a glass network modifier. We have found, however, that partial or complete substitution of $Pr_2O_3$ for $La_2O_3$ results in pH glass compositions having reduced surface resistivity, as well as reduced bulk resistivity. Similarly, we have found that the electrical resistance properties of glasses containing both $La_2O_3$ and $Ta_2O_5$ can be improved (i.e., lowered) by replacing part of the $Ta_2O_5$ by $Nb_2O_5$. Frequently, the simultaneous addition of $UO_2$ gives additional advantages in workability and reduced bulk electrical resistance. Finally, $Cs_2O$ is incorporated in pH glass compositions to reduce sodium error. However, $Rb_2O$ can be substituted for $Cs_2O$ without adverse effects, and sometimes with advantage.

Some of the properties of glasses at the claimed compositional limits are shown by the glasses of Examples 7–11, inclusive. Glasses containing less than about 30 mole percent $Li_2O$ are likely to have undesirably high electrical resistance properties which render such glasses unsuitable for use in electrodes having small or thick sensors. On the other hand, glasses containing greater than about 37 mole percent $Li_2O$ are likely to have poor workability and durability. Compositions exceeding 4 mole percent in $Cs_2O$ or $Rb_2O$ are likely to have excessive electrical resistivity properties. Glasses containing less than the minimum required amounts of $La_2O_3$ and $Pr_2O_3$ or $Ta_2O_5$ and $Nb_2O_5$ are likely to have excessive alkali error or poorer workability, whereas glasses containing more than the maximum amounts allowed are likely to have excessive electrical resistance properties or poor melt characteristics. While the performance of some of the glasses at or near the claimed compositional limits would be unsatisfactory for use in full-range pH electrodes, some of the adversely-affected properties such as alkali error and limited range would not necessarily be a liability in less stringent applications such as the instrumental measurement of blood pH where such glasses could be used to advantage.

Having thus disclosed the invention, many variations thereof will be apparent to those having ordinary skill in the art without departing from the spirit and scope of the invention.

What is claimed is:

1. A glass composition for use in pH-responsive glass electrodes consisting essentially of (in mole percent on the oxide basis):
    a. from about 30 to about 37 mole percent $Li_2O$;
    b. from 0 to about 4 mole percent of at least one oxide selected from the group consisting of $Cs_2O$ and $Rb_2O$;
    c. from about 2 to about 12 mole percent of at least one oxide selected from the group consisting of $La_2O_3$ and $Pr_2O_3$;
    d. from about 2 to about 10 mole percent of at least one oxide selected from the group consisting of $Ta_2O_5$ and $Nb_2O_5$;
    e. from 0 to about 4 mole percent $UO_2$; and
    f. the balance $SiO_2$;

with the proviso that there is present in the composition at least about 2 mole percent of at least one oxide selected from the group consisting of $Pr_2O_3$ and $Nb_2O_5$.

2. The composition of claim 1 which consists essentially of:
    a. from about 30 to about 37 mole percent $Li_2O$;
    b. from 0 to about 4 mole percent of at least one oxide selected from the group consisting of $Cs_2O$ and $Rb_2O$;
    c. from 0 to about 6 mole percent $La_2O_3$;
    d. from about 2 to about 8 mole percent $Pr_2O_3$;
    e. from about 2 to about 8 mole percent of at least one oxide selected from the group consisting of $Ta_2O_5$ and $Nb_2O_5$;
    f. from 0 to about 4 mole percent $UO_2$; and
    g. the balance $SiO_2$;

with the proviso that the sum of the mole percentages of $La_2O_3$ and $Pr_2O_3$ is equal to or less than about 12.

3. The composition of claim 2 which consists essentially of:
    a. from about 31 to about 35 mole percent $Li_2O$;
    b. from about 1 to about 3 mole percent of at least one oxide selected from the group consisting of $Cs_2O$ and $Rb_2O$;
    c. from 0 to about 4 mole percent $La_2O_3$;
    d. from about 3 to about 6 mole percent $Pr_2O_3$;
    e. from about 4 to about 8 mole percent of at least one oxide selected from the group consisting of $Ta_2O_5$ and $Nb_2O_5$;
    f. from 0 to about 2 mole percent $UO_2$; and
    g. the balance $SiO_2$.

4. The composition of claim 3 which consists essentially of 33 mole percent $Li_2O$, 2 mole percent $Cs_2O$, 6 mole percent $Pr_2O_3$, 6 mole percent $Ta_2O_5$, and 53 mole percent $SiO_2$.

5. The composition of claim 3 which consists essentially of 33 mole percent $Li_2O$, 2 mole percent $Cs_2O$, 6 mole percent $Pr_2O_3$, 6 mole percent $Ta_2O_5$, 2 mole percent $UO_2$, and 51 mole percent $SiO_2$.

6. The composition of claim 3 which consists essentially of 33 mole percent $Li_2O$, 2 mole percent $Cs_2O$, 3 mole percent $La_2O_3$, 3 mole percent $Pr_2O_3$, 6 mole percent $Ta_2O_5$, and 53 mole percent $SiO_2$.

7. The composition of claim 1 which consists essentially of:
   a. from about 30 to about 37 mole percent $Li_2O$;
   b. from 0 to about 4 mole percent of at least one oxide selected from the group consisting of $Cs_2O$ and $Rb_2O$;
   c. from about 2 to about 8 mole percent $La_2O_3$;
   d. from 0 to about 6 mole percent $Ta_2O_5$;
   e. from about 2 to about 8 mole percent $Nb_2O_5$;
   f. from 0 to about 4 mole percent $UO_2$; and
   g. the balance $SiO_2$;

with the proviso that the sum of the mole percentages of $Ta_2O_5$ and $Nb_2O_5$ is equal to or less than about 10.

8. The composition of claim 7 which consists essentially of:
   a. from about 31 to about 35 mole percent $Li_2O$;
   b. from about 1 to about 3 mole percent of at least one oxide selected from the group consisting of $Cs_2O$ and $Rb_2O$;
   c. from about 3 to about 7 mole percent $La_2O_3$;
   d. from 0 to about 4 mole percent $Ta_2O_5$;
   e. from about 2 to about 7 mole percent $Nb_2O_5$;
   f. from 0 to about 2 mole percent $UO_2$; and
   g. the balance $SiO_2$;

with the proviso that the sum of the mole percentages of $Ta_2O_5$ and $Nb_2O_5$ is equal to or less than about 10.

9. The composition of claim 8 which consists essentially of 33 mole percent $Li_2O$, 2 mole percent $Cs_2O$, 6 mole percent $La_2O_3$, 3 mole percent $Ta_2O_5$, 3 mole percent $Nb_2O_5$, and 53 mole percent $SiO_2$.

10. The composition of claim 8 which consists essentially of 33 mole percent $Li_2O$, 2 mole percent $Cs_2O$, 6 mole percent $La_2O_3$, 6 mole percent $Nb_2O_5$, and 53 mole percent $SiO_2$.

11. The composition of claim 8 which consists essentially of 33 mole percent $Li_2O$, 2 mole percent $Rb_2O$, 6 mole percent $La_2O_3$, 6 mole percent $Nb_2O_5$, and 53 mole percent $SiO_2$.

12. A glass electrode having a pH-responsive membrane of glass having a composition consisting essentially of (in mole percent on the oxide basis):
   a. from about 30 to about 37 mole percent $Li_2O$;
   b. from 0 to about 4 mole percent of at least one oxide selected from the group consisting of $Cs_2O$ and $Rb_2O$;
   c. from about 2 to about 12 mole percent of at least one oxide selected from the group consisting of $La_2O_3$ and $Pr_2O_3$;
   d. from about 2 to about 10 mole percent of at least one oxide selected from the group consisting of $Ta_2O_5$ and $Nb_2O_5$;
   e. from 0 to about 4 mole percent $UO_2$; and
   f. the balance $SiO_2$;

with the proviso that there is present in the composition at least about 2 mole percent of at least one oxide selected from the group consisting of $Pr_2O_3$ and $Nb_2O_5$.

13. The electrode of claim 12, in which the pH-responsive membrane of glass has a composition consisting essentially of:
   a. from about 30 to about 37 mole percent $Li_2O$;
   b. from 0 to about 4 mole percent of at least one oxide selected from the group consisting of $Cs_2O$ and $Rb_2O$;
   c. from 0 to about 6 mole percent $La_2O_3$;
   d. from about 2 to about 8 mole percent $Pr_2O_3$;
   e. from about 2 to about 8 mole percent of at least one oxide selected from the group consisting of $Ta_2O_5$ and $Nb_2O_5$;
   f. from 0 to about 4 mole percent $UO_2$; and
   g. the balance $SiO_2$;

with the proviso that the sum of the mole percentages of $La_2O_3$ and $Pr_2O_3$ is equal to or less than about 12.

14. The electrode of claim 13, in which the pH-responsive membrane of glass has a composition consisting essentially of:
   a. from about 31 to about 35 mole percent $Li_2O$;
   b. from about 1 to about 3 mole percent of at least one oxide selected from the group consisting of $Cs_2O$ and $Rb_2O$;
   c. from 0 to about 4 mole percent $La_2O_3$;
   d. from about 3 to about 6 mole percent $Pr_2O_3$;
   e. from about 4 to about 8 mole percent of at least one oxide selected from the group consisting of $Ta_2O_5$ and $Nb_2O_5$;
   f. from 0 to about 2 mole percent $UO_2$; and
   g. the balance $SiO_2$.

15. The electrode of claim 14, in which the pH-responsive membrane of glass has a composition consisting essentially of 33 mole percent $Li_2O$, 2 mole percent $Cs_2O$, 6 mole percent $Pr_2O_3$, 6 mole percent $Ta_2O_5$, and 53 mole percent $SiO_2$.

16. The electrode of claim 14, in which the pH-responsive membrane of glass has a composition consisting essentially of 33 mole percent $Li_2O$, 2 mole percent $Cs_2O$, 6 mole percent $Pr_2O_3$, 6 mole percent $Ta_2O_5$, 2 mole percent $UO_2$, and 51 mole percent $SiO_2$.

17. The electrode of claim 14, in which the pH-responsive membrane of glass has a composition consisting essentially of 33 mole percent $Li_2O$, 2 mole percent $Cs_2O$, 3 mole percent $La_2O_3$, 3 mole percent $Pr_2O_3$, 6 mole percent $Ta_2O_5$, and 53 mole percent $SiO_2$.

18. The electrode of claim 12, in which the pH-responsive membrane of glass has a composition consisting essentially of:
   a. from about 30 to about 37 mole percent $Li_2O$;
   b. from 0 to about 4 mole-percent of at least one oxide selected from the group consisting of $Cs_2O$ and $Rb_2O$;
   c. from about 2 to about 8 mole percent $La_2O_3$;
   d. from 0 to about 6 mole percent $Ta_2O_5$;
   e. from about 2 to about 8 mole percent $Nb_2O_5$;
   f. from 0 to about 4 mole percent $UO_2$; and
   g. the balance $SiO_2$;

with the proviso that the sum of the mole percentages of $Ta_2O_5$ and $Nb_2O_5$ is equal to or less than about 10.

19. The electrode of claim 18, in which the pH-responsive membrane of glass has a composition consisting essentially of:
   a. from about 31 to about 35 mole percent $Li_2O$;
   b. from about 1 to about 3 mole percent of at least one oxide selected from the group consisting of $Cs_2O$ and $Rb_2O$;
   c. from about 3 to about 7 mole percent $La_2O_3$;
   d. from 0 to about 4 mole percent $Ta_2O_5$;
   e. from about 2 to about 7 mole percent $Nb_2O_5$;
   f. from 0 to about 2 mole percent $UO_2$; and
   g. the balance $SiO_2$;

with the proviso that the sum of the mole percentages of $Ta_2O_5$ and $Nb_2O_5$ is equal to or less than about 10.

20. The electrode of claim 19, in which the pH-responsive membrane of glass has a composition consisting essentially of 33 mole percent $Li_2O$, 2 mole percent $Cs_2O$, 6 mole percent $La_2O_3$, 3 mole percent $Ta_2O_5$, 3 mole percent $Nb_2O_5$, and 53 mole percent $SiO_2$.

21. The electrode of claim 19, in which the pH-responsive membrane of glass has a composition consisting essentially of 33 mole percent $Li_2O$, 2 mole percent $Cs_2O$, 6 mole precent $La_2O_3$, 6 mole percent $Nb_2O_5$, and 53 mole precent $SiO_2$.

22. The electrode of claim 19, in which the pH-responsive membrane of glass has a composition consisting essentially of 33 mole percent $Li_2O$, 2 mole percent $Rb_2O$, 6 mole percent $La_2O_3$, 6 mole percent $Nb_2O_5$, and 53 mole percent $SiO_2$.

* * * * *